United States Patent
Ben Shoshan et al.

(10) Patent No.: US 10,935,484 B2
(45) Date of Patent: Mar. 2, 2021

(54) AUTOMATED ASSESSMENT OF SPERM SAMPLES

(71) Applicant: G.M.S Global Mobile Solutions Ltd., Caesarea (IL)

(72) Inventors: Assaf Ben Shoshan, Kibbutz Barkai (IL); Vitaly Strongin, Nesher (IL); Lior Shriki, Haifa (IL); Marcia Deutsch, Los Angeles, CA (US); Benihu Cohen, Nesher (IL)

(73) Assignee: MES MEDICAL ELECTRONIC SYSTEMS LTD., Caesarea (IL)

( * ) Notice: Subject to any disclaimer, the term of this patent is extended or adjusted under 35 U.S.C. 154(b) by 0 days.

(21) Appl. No.: 16/438,484

(22) Filed: Jun. 12, 2019

(65) Prior Publication Data
US 2019/0293545 A1   Sep. 26, 2019

Related U.S. Application Data

(63) Continuation of application No. 15/037,050, filed as application No. PCT/IB2014/066716 on Dec. 9, 2014, now abandoned.
(Continued)

(51) Int. Cl.
| | |
|---|---|
| *G01N 15/14* | (2006.01) |
| *G01N 15/06* | (2006.01) |
| *G01N 15/10* | (2006.01) |
| *G06K 9/00* | (2006.01) |
| *H04M 1/725* | (2021.01) |
| *H04B 1/3888* | (2015.01) |
| *H04M 1/02* | (2006.01) |
| *H04N 5/225* | (2006.01) |

(Continued)

(52) U.S. Cl.
CPC ........ *G01N 15/1463* (2013.01); *C12M 21/06* (2013.01); *C12M 23/22* (2013.01); *C12M 41/36* (2013.01); *G01N 15/06* (2013.01); *G01N 15/0606* (2013.01); *G06K 9/00134* (2013.01); *H04B 1/3888* (2013.01); *H04M 1/0264* (2013.01); *H04M 1/72527* (2013.01); *H04N 5/2254* (2013.01); *H04N 5/2256* (2013.01); *G01N 2015/0693* (2013.01); *G01N 2015/1006* (2013.01); *G01N 2015/1075* (2013.01); *G01N 2015/1486* (2013.01)

(58) Field of Classification Search
USPC ....... 382/128, 133, 162, 164, 165, 168, 170, 382/171, 190, 192, 194, 195, 224, 225
See application file for complete search history.

(56) References Cited

U.S. PATENT DOCUMENTS 3,638,188 A * 1/1972 Pincoffs .................. G06K 9/46
 382/225
3,829,216 A * 8/1974 Persidsky .............. G02B 21/34
 356/36

(Continued)

OTHER PUBLICATIONS

U.S. Appl. No. 16/379,851 office action dated Dec. 9, 2019.

*Primary Examiner* — Kara E. Geisel
*Assistant Examiner* — Jarreas C Underwood
(74) *Attorney, Agent, or Firm* — Fresh IP PLC; Clifford D. Hyra; Aubrey Y Chen

(57) ABSTRACT

A method for testing includes capturing a sequence of video images of a sample comprising semen. The sequence of video images is analyzed by a processor so as to compute and output a motile sperm concentration of the sample.

20 Claims, 6 Drawing Sheets

Related U.S. Application Data

(60) Provisional application No. 61/914,980, filed on Dec. 12, 2013.

(51) Int. Cl.
*C12M 3/00* (2006.01)
*C12M 1/00* (2006.01)
*C12M 1/34* (2006.01)

(56) References Cited

U.S. PATENT DOCUMENTS

| | | | |
|---|---|---|---|
| 4,804,600 A | 2/1989 | Kato et al. | |
| 4,824,247 A * | 4/1989 | True | A61B 10/00 356/244 |
| 4,908,872 A * | 3/1990 | Toriu | G06K 9/4609 382/197 |
| 5,031,099 A * | 7/1991 | Kettler | G01N 15/1468 382/133 |
| 6,173,077 B1 * | 1/2001 | Trew | H04N 19/51 382/236 |
| 6,272,233 B1 * | 8/2001 | Takeo | G06T 5/20 128/922 |
| 7,081,940 B2 | 7/2006 | Suzuki | |
| 7,279,063 B2 | 10/2007 | Yokajty et al. | |
| 7,718,124 B2 | 5/2010 | Simmet | |
| 7,831,599 B2 * | 11/2010 | Das | G06F 16/58 707/737 |
| 9,696,535 B2 * | 7/2017 | Prakash | G01N 21/01 |
| 9,784,961 B2 * | 10/2017 | Wooder | G02B 21/0004 |
| 2002/0114577 A1 | 8/2002 | Kondo et al. | |
| 2003/0031366 A1 * | 2/2003 | Li | G06K 9/38 382/206 |
| 2005/0136549 A1 * | 6/2005 | Gholap | G06K 9/0014 436/501 |
| 2006/0039603 A1 * | 2/2006 | Koutsky | G06T 7/90 382/165 |
| 2006/0067187 A1 | 3/2006 | Yang et al. | |
| 2007/0024707 A1 * | 2/2007 | Brodsky | H04N 5/232 348/143 |
| 2007/0184431 A1 * | 8/2007 | Armogida | G06K 9/0014 435/4 |
| 2007/0298454 A1 * | 12/2007 | Green | G06T 7/0012 435/34 |
| 2008/0144945 A1 * | 6/2008 | Merlet | G06K 9/00 382/225 |
| 2009/0238423 A1 * | 9/2009 | Rigler | G01N 35/00871 382/128 |
| 2010/0172555 A1 * | 7/2010 | Hasezawa | G06K 9/00127 382/128 |
| 2011/0013821 A1 * | 1/2011 | Mimura | G06T 7/0016 382/133 |
| 2011/0294543 A1 * | 12/2011 | Lapstun | H04N 1/00129 455/556.1 |
| 2012/0148141 A1 * | 6/2012 | Ozcan | G03H 1/0866 382/133 |
| 2013/0163844 A1 * | 6/2013 | Ozaki | G06K 9/0014 382/133 |
| 2013/0194410 A1 * | 8/2013 | Topman | G06K 9/0014 348/79 |
| 2013/0273524 A1 * | 10/2013 | Ehrenkranz | G01N 15/1463 435/5 |
| 2013/0314526 A1 * | 11/2013 | Yasuda | G01N 15/1475 348/79 |
| 2014/0212959 A1 * | 7/2014 | Matsuura | G01N 15/1463 435/288.7 |
| 2014/0267670 A1 * | 9/2014 | Tipgunlakant | G02B 21/16 348/79 |
| 2014/0356864 A1 * | 12/2014 | Khan | G01N 21/25 435/5 |

\* cited by examiner

AUTOMATED ASSESSMENT OF SPERM SAMPLES

CROSS-REFERENCE TO RELATED APPLICATIONS

This application is a continuation of U.S. patent application Ser. No. 15/037,050, filed May 17, 2016, in the national phase of PCT Patent Application PCT/IB2014/066716, filed Dec. 9, 2014, which claims the benefit of U.S. Provisional Patent Application 61/914,980, filed Dec. 12, 2013, which is incorporated herein by reference.

FIELD OF THE INVENTION

The present invention relates generally to optical inspection of samples, and specifically to automated methods and devices for capture and analysis of electronic images of samples.

BACKGROUND

Infertility is a common yet complex problem, affecting approximately 10-15% of couples attempting to conceive a child. In up to one third of these cases, the problem is at least in part related to male reproductive issues. Among these issues, low sperm motility is commonly associated with infertility. A qualitative assessment of motile sperm can be made by visually evaluating the motion of the sperm in the sample under the microscope. These microscope systems are generally expensive, however, and are not suitable for use by inexperienced personnel. This sort of visual evaluation can produce inconsistent results even when used by well-trained personnel.

A number of devices and methods have been developed for automated sperm motility testing. For example, U.S. Patent Application Publication 2014/0254004 describes test kits for assessing male fertility, which include a sample holder defining an object plane, a lens, and a two-dimensional light sensor defining an image plane arranged along a common linear axis. The test kit may have a housing with a maximum linear dimension of no more than 100 mm. Processing circuitry may be provided that is configured to produce a sperm count and/or sperm motility measurements by processing image data from the two-dimensional light sensor.

Nearly all mobile telephones currently on sale include built-in cameras, which may be used in various applications. For example, U.S. Patent Application Publication 2011/0292198 describes a microscope accessory for attachment to a mobile phone having a display positioned in a first face and a camera positioned in an opposite second face. The microscope accessory includes engagement features for releasably attaching the microscope accessory to the mobile phone, and an optical assembly having a first mirror positioned to be offset from the camera, a second mirror positioned for alignment with the camera, and a microscope lens positioned in the optical path. The optical assembly is matched with the camera, such that a surface is in focus when the mobile phone lies flat against the surface.

SUMMARY

Some of the embodiments of the present invention that are described hereinbelow provide devices and methods that make use of the imaging and processing capabilities of a mobile computing device, such as a Smartphone, to perform microscopic inspection and automated assessment of a sample.

There is therefore provided, in accordance with an embodiment of the present invention, an optical device, including a case, which is configured to fit over at least a part of a mobile computing device having first and second faces and including a light source, which emits a beam of illumination through an exit aperture, and a camera module, which captures images through an entrance aperture, wherein both the entrance and exit apertures open through the second face of the mobile computing device. A receptacle in the case is configured to receive and position a sample in proximity to the second face of the mobile computing device within a field of view of the camera module. Illumination optics are configured to receive and turn the beam emitted by the light source so as to back-illuminate the sample while the camera module captures one or more images of the back-illuminated sample.

In the disclosed embodiments, the light source directs the beam away from the second face of the mobile computing device, and the illumination optics include at least one reflector, which is configured to reflect the beam back toward the second face. The device may include a pair of reflective surfaces, each configured to turn the beam by 90°.

In some embodiments, the device includes a lens mounted in the case in a location between the sample and the entrance aperture and configured so that the sample is located within a focal range of the camera module. Typically, the lens is configured to magnify the one or more images captured by the camera module. In a disclosed embodiment, the lens includes a ball lens, having wings attached thereto for mounting in the case.

In some embodiments, the apparatus includes a transparent sample holder, which is configured to receive the sample and to be positioned within the receptacle so as to position the sample securely in the field of view of the camera. When the sample is liquid, the sample holder typically includes a slide having a depression formed therein to contain the sample and a cover slip fixed over the depression.

There is also provided, in accordance with an embodiment of the present invention, testing apparatus, including a mobile computing device having first and second faces and including a light source, which emits a beam of illumination through an exit aperture, and a camera module, which captures images through an entrance aperture, wherein both the entrance and exit apertures open through the second face of the mobile computing device. The apparatus further includes an optical device as described above, which is configured to fit over the mobile computing device so that the receptacle positions the sample within the field of view of the camera module, and the illumination optics are aligned with the light source.

In a disclosed embodiment, the mobile computing device is a Smartphone.

Typically, the mobile computing device includes a processor, which is configured to process the captured images so as to analyze a property of the sample. In some embodiments, the sample includes semen, and the processor is configured to analyze a motility characteristic of spermatozoa in the semen.

Additionally or alternatively, the mobile computing device includes a display screen on the first face of the mobile computing device, and the processor is configured to present an assessment of the property on the display screen.

There is additionally provided, in accordance with an embodiment of the present invention, a sample holder, including a slide, containing a depression in a surface of the slide, and a cover slip, which is fixed to the slide over the depression so as to define a sample chamber, while leaving a loading area of the depression uncovered, so that a liquid sample deposited in the loading area is drawn into the sample chamber by capillary action.

In a disclosed embodiment, the slide is molded to define at least one first groove, into which an adhesive is inserted in order to fix the cover slip to the slide, and at least one second groove located between the at least one first groove and the depression so as to prevent overflow of the adhesive from the at least one first groove into the sample chamber.

There is further provided, in accordance with an embodiment of the present invention, a method for testing, which includes inserting a sample into a transparent sample holder and inserting the transparent sample holder with the sample into an optical adapter. The optical adapter is fitted over a mobile computing device that includes a light source, which emits a beam of illumination through an exit aperture, and a camera module, which captures images through an entrance aperture, so that the sample is positioned within a field of view of the camera module. An image of the sample in the optical adapter is captured using the camera module while illuminating the sample with the beam emitted by the light source. The captured image is analyzed in the mobile computing device so as to compute and output an assessment of the sample.

In some embodiments, the sample is liquid, and the sample holder includes a slide having a depression formed therein to contain the sample and a cover slip fixed over the depression. In a disclosed embodiment, the cover slip is fixed to the slide over the depression so as to define a sample chamber, while leaving a loading area of the depression uncovered, and inserting the sample includes depositing the sample in the loading area so that the liquid is drawn into the sample chamber by capillary action.

In a disclosed embodiment, the mobile computing device is a Smartphone, and analyzing the captured image includes processing the captured image using application software running on a processor in the smartphone.

In some embodiments, the sample includes semen, and analyzing the captured image includes assessing a motility characteristic of spermatozoa in the semen, for example by computing a motile sperm concentration.

The present invention will be more fully understood from the following detailed description of the embodiments thereof, taken together with the drawings in which:

DETAILED DESCRIPTION OF EMBODIMENTS

Figure 1:
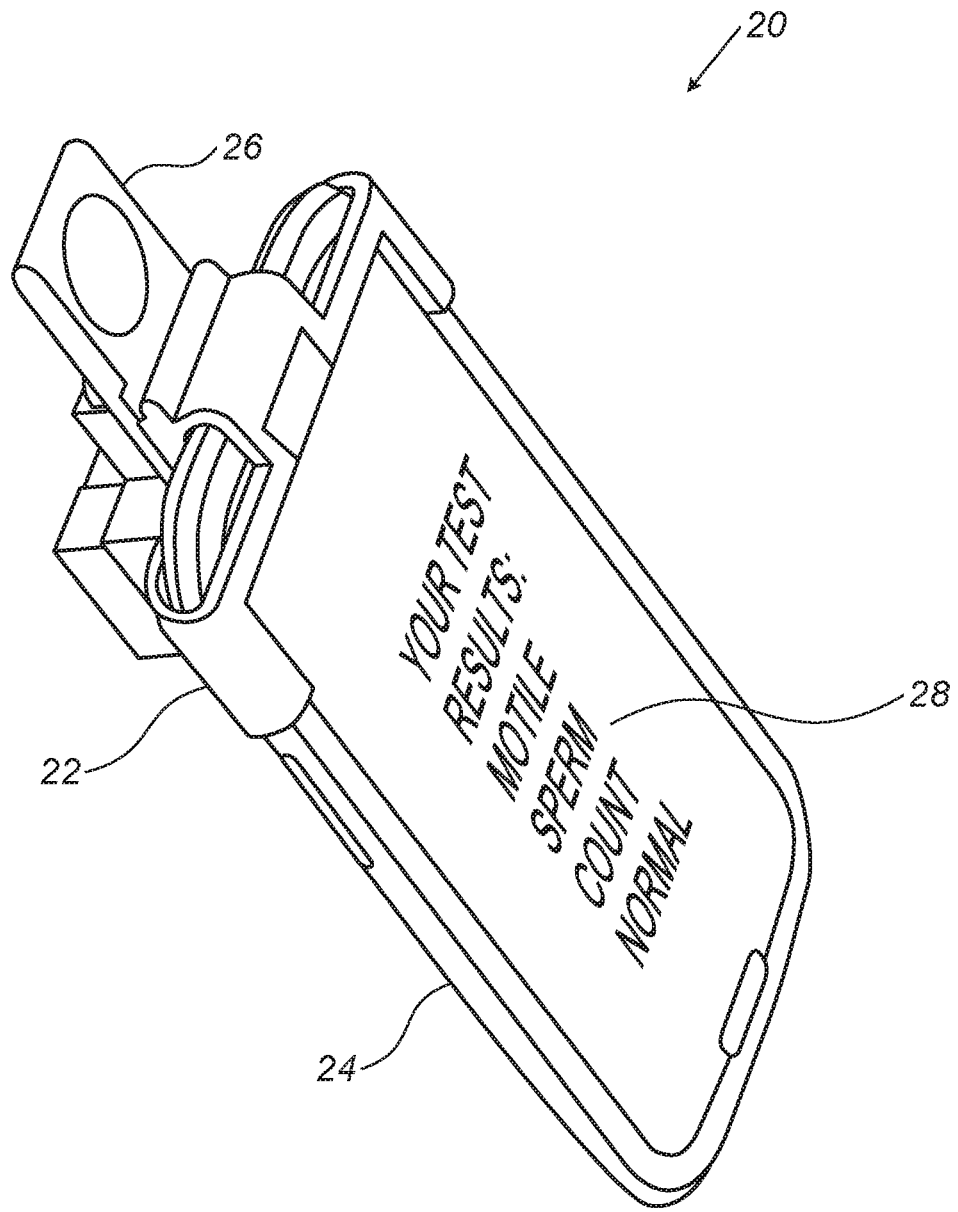
FIG. 1 is a schematic, pictorial illustration of testing apparatus, in accordance with an embodiment of the present invention.

In view of the high incidence of male fertility problems, sperm testing should be performed at an early stage in most cases in which a couple has difficulty in conceiving. Such testing requires, however, that the man either ejaculate a semen sample at the laboratory, which can be difficult and embarrassing, or rush the sample from his home to the laboratory, with the risk that the sperm may die in transit.

Embodiments of the present invention that are described herein address this problem by providing an automated sperm testing apparatus that can be operated conveniently and reliably in the privacy of one's home. The apparatus comprises an optical adapter, which fits onto an existing mobile computing device, such as a smart phone, and converts the device into a video microscope. The apparatus takes advantage of the existing resources of the mobile computing device, including camera (and its internal optics), illumination source, processor and display screen, and thus provides a low-cost solution that enables the user to test his semen at home at any stage, even before going to see a doctor.

In the disclosed embodiments, a clip-on optical adapter device comprises a case, which fits over at least the part of a mobile computing device, such as a Smartphone, where the light source and camera module are located. The case of the adapter device has a receptacle for a sample, such as a semen sample or other liquid sample, contained in a suitable sample holder, such as a transparent slide. When inserted into this receptacle, the sample is positioned within the field of view and focal range of the camera module, in proximity to the face of the mobile computing device where the entrance and exit apertures are located. In the disclosed embodiments, the desired focus and magnification of the sample are achieved with the assistance of internal optics in the adapter device, as described below.

To capture a suitable electronic image of the sample for analysis, it is desirable that the sample be back-illuminated. In all common Smartphones, as well as other, similar devices, however, the exit aperture of the light source and the entrance aperture of the camera module are located on the same face of the device, not facing one another as required for back-illumination. A separate light source could be provided for this purpose, but this approach increases the size and cost of the adapter and also requires it to provide power to the light source.

Instead, the disclosed embodiments of the present invention exploit the existing light source in the mobile computing device itself, using illumination optics in the case of the adapter device to receive and turn the beam emitted by the light source so as to back-illuminate the sample. Thus, the camera module (with the assistance of the optics in the adapter device) captures back-illuminated images of the sample, which are processed by the mobile computing device in order to compute and output an assessment of the sample. Typically, the adapter device also comprises a lens mounted in the case in a location between the sample and the entrance aperture of the camera module, which magnifies the images captured by the camera module.

A clip-on adapter of this sort, which takes advantage of the light source and camera module in a Smartphone or other mobile computing device, can be useful in various methods for automated testing. Thus, embodiments of the present invention also provide a method in which a sample is inserted into a transparent sample holder, the transparent sample holder with the sample is inserted into an optical adapter, and the optical adapter is fitted over a mobile computing device. (Alternatively, the adapter may first be fitted over the mobile computing device, after which the sample holder is inserted into the adapter.) The camera module captures one or more electronic images of the sample, which is illuminated by the beam emitted by the light source in the Smartphone. An application program running on the mobile computing device actuates the light source and camera module, and causes the processor in the device to analyze the images so as to compute and output an assessment of the sample.

In a disclosed embodiment, the sample comprises semen, as noted above, and the processor assesses the motility of the spermatozoa in the semen. Advantageously, the processor may compute and output an assessment of a motility characteristic of the spermatozoa, such as the motile sperm concentration (MSC, also referred to in some publications as motile sperm count), which is the product of the sperm concentration multiplied by the percent motility of the sperm (divided by 100). Because MSC integrates these two parameters, it gives a better screening indication for fertility problems than either sperm concentration or motility alone.

FIG. 1 is a schematic, pictorial illustration of testing apparatus 20, in accordance with an embodiment of the present invention. Apparatus 20 comprises a mobile computing device in the form of a Smartphone 24, which may be of any suitable type that is known in the art. An optical adapter device 22 fits over the upper part of Smartphone 24. A sample holder, in the form of a test slide 26, is inserted into the adapter device, so that the sample that it contains is positioned within the field of view and focal range of the camera module in Smartphone 24 (as shown in the figures that follow, which include the internal optics in adapter device 22).

The processor (not shown) in Smartphone 24 analyzes images captured by the camera module in order to make an assessment of the sample, and outputs the assessment to a display screen 28. The images captured by the camera module are referred to interchangeably herein as "electronic images" or "video images." For the sake of clarity in the description that follows, the term "first face" in reference to Smartphone 24 refers to the side of the Smartphone on which display screen 28 is located, while the reverse face, facing into the page in FIG. 1, is referred to as the second face.

Although the present embodiment and the figures in this patent application refer to a particular type of Smartphone, the features of this embodiment may be adapted, mutatis mutandis, to work with Smartphones of other types and designs, as well as with other mobile devices having suitable imaging and computing capabilities, such as tablet and laptop computers. All such alternative implementations are considered to be within the scope of the present invention.

Figure 2:
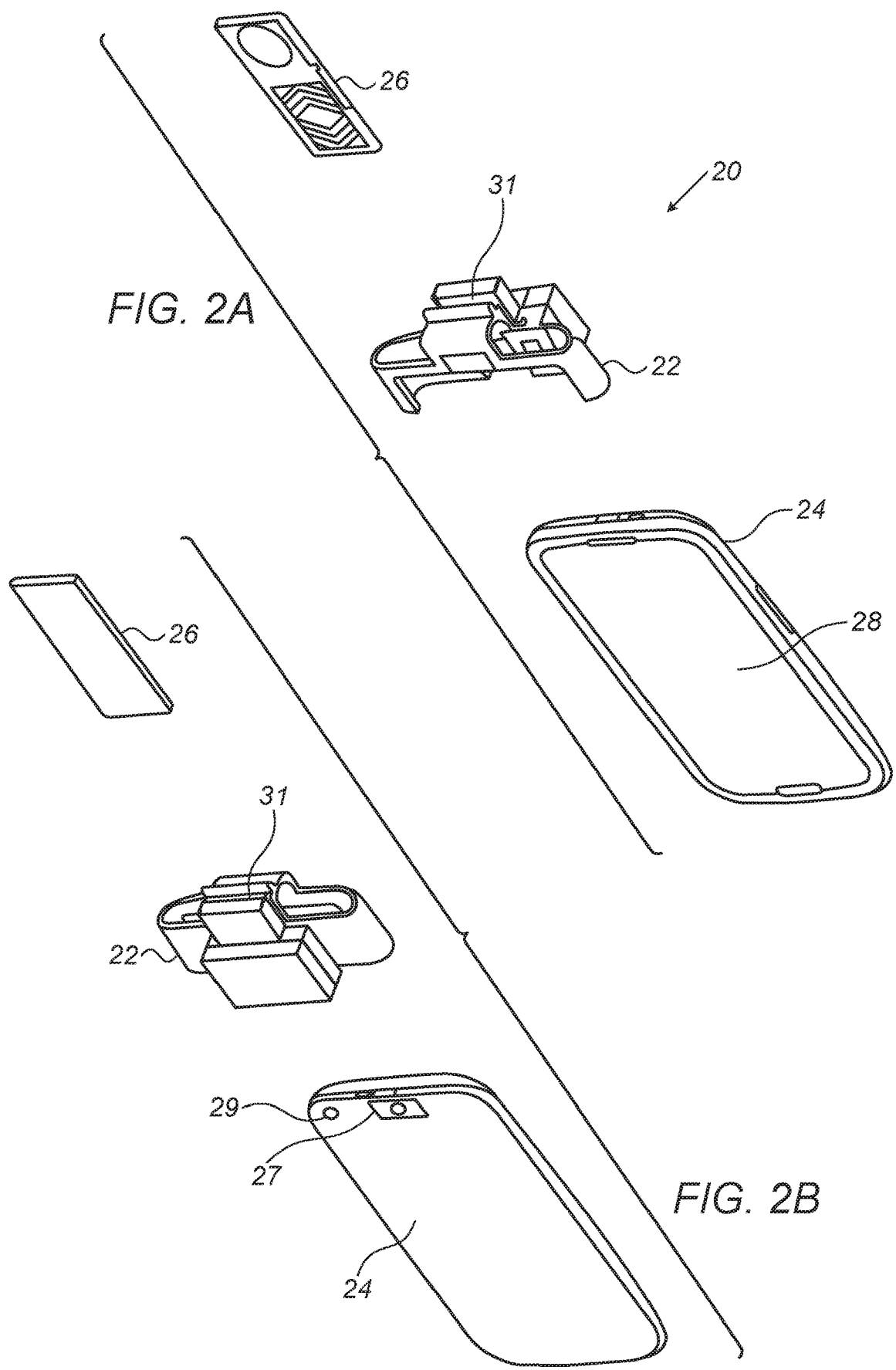
FIGS. 2A and 2B are schematic exploded views of the apparatus of FIG. 1, shown from the front and rear sides of the apparatus, respectively, in accordance with an embodiment of the present invention.

FIGS. 2A and 2B are schematic exploded views of apparatus 20, shown from the front and rear sides, respectively, in accordance with an embodiment of the present invention. As noted earlier, FIG. 2A shows the "first face" of Smartphone 24, while FIG. 2B shows the "second face." The Smartphone comprises a camera module 27 and a light source 29, which respectively have an entrance aperture and an exit aperture alongside one another in the second face of the Smartphone. Adapter device 22 fits over the end of Smartphone 24 and covers the entrance and exist apertures of camera module 27 and light source 29.

Test slide 26 fits into a receptacle 31, which is shaped as a slot in the case of adapter device 22. Alternatively, receptacle 31 may be configured to receive samples and sample holders, made of appropriate transparent materials, of any suitable size and shape.

Figure 3:
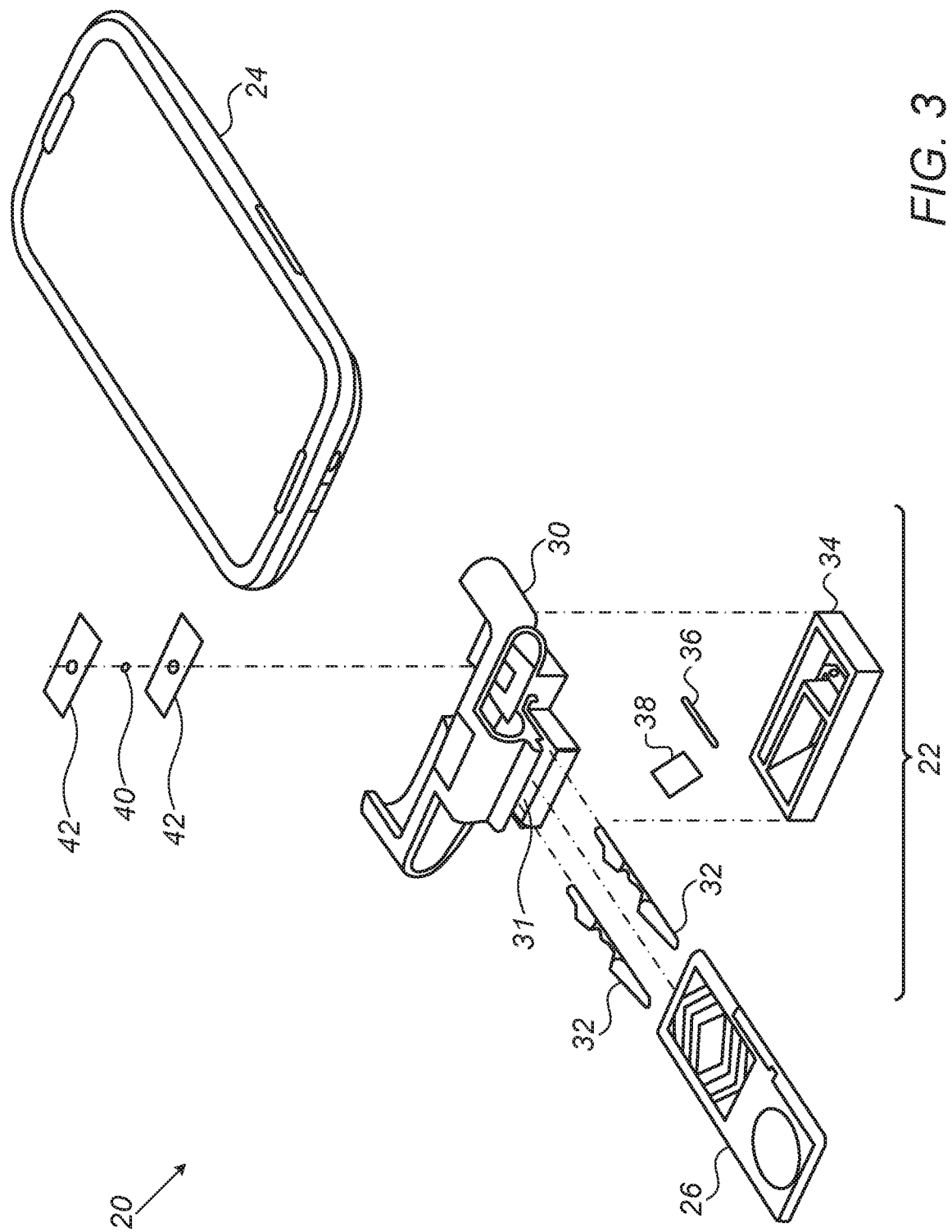
FIG. 3 is a schematic exploded view of a microscopy adapter for a mobile computing device used in the apparatus of FIG. 1, in accordance with an embodiment of the present invention.

FIG. 3 is a schematic exploded view of adapter device 22, in accordance with an embodiment of the present invention. Device 22 comprises a case 30, which is typically made from molded plastic and includes a slot for receptacle 31. Springs 32 are fitted into the case in order to hold slide 26 securely and precisely in the receptacle, with the sample in the field of view and focal range of camera module 27. A mirror holder 34 fits onto the back of case 30 and holds a pair of mirrors 36 and 38, whose operation as illumination optics in device 22 is described below with reference to FIG. 4.

A ball lens 40, held between a pair of lens holders 42, is mounted in case 30 in a location between the sample held by slide 26 and the entrance aperture of camera module 27. Springs 32 hold slide 26 at a fixed, accurate distance from lens 40. Lens 40 serves to magnify the images of the sample that are captured by the camera module. Lens holders 42 are shaped as wings, extending out to either side of ball lens 40, without occluding the small optical aperture of the ball lens. Alternatively, the ball lens and wings may be molded together out of a single piece of optical plastic or glass. Typically, ball lens 40 is about 2 mm in diameter, although larger or smaller elements may alternatively be used. Further alternatively, ball lens 40 may be replaced by other magnifying optics, such as a miniature simple lens (either spherical or aspheric) or even a compound lens, depending on the desired magnification and other optical requirements.

Figure 4:
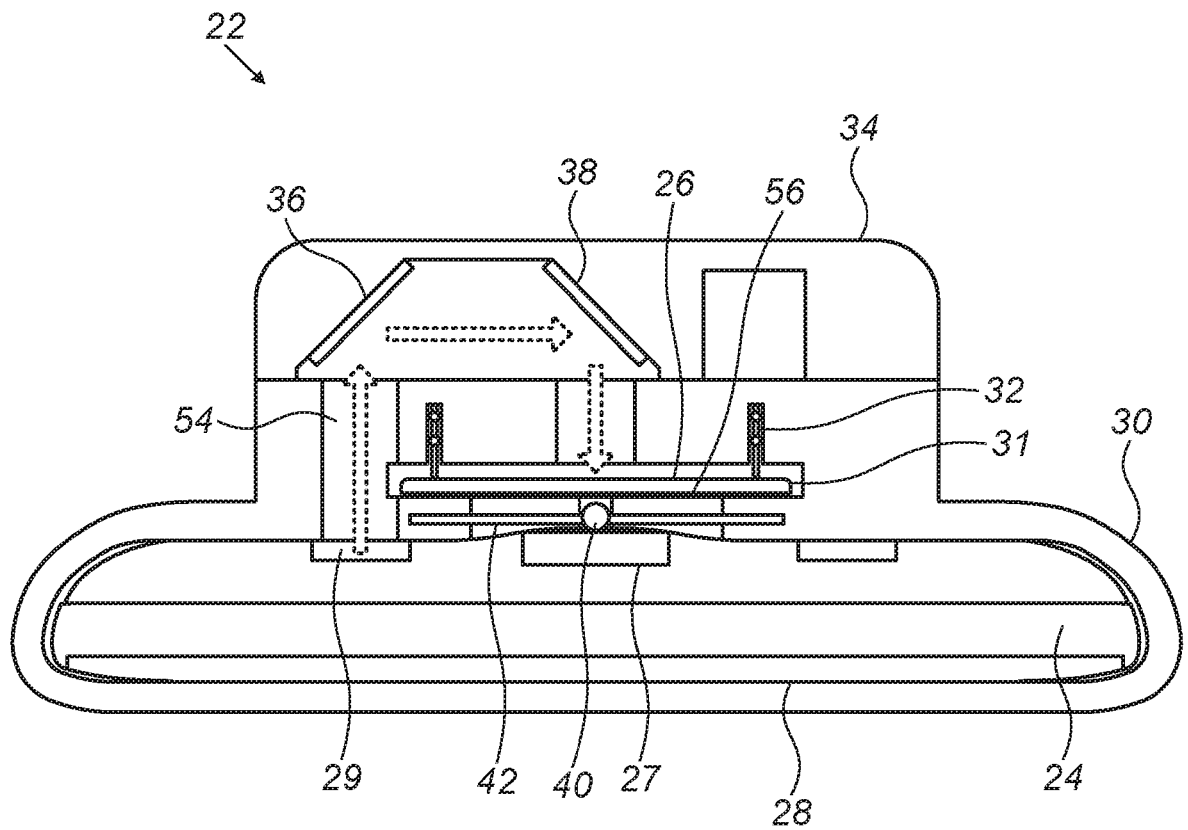
FIG. 4 is a schematic sectional view showing details of the apparatus of FIG. 1, in accordance with an embodiment of the present invention.

FIG. 4 is a schematic sectional view showing details of apparatus 20, and particularly of adapter device 22, in accordance with an embodiment of the present invention. This figure illustrates the functionality of the elements that were described above with reference to FIG. 3. Light source 29 directs a beam 54 of illumination away from the second face of Smartphone 24. Beam 54 is reflected back toward the entrance aperture of camera module 27 in the second face of the Smartphone by the reflective surfaces of mirrors 36 and 38, each of which turns the beam by 90°. In the pictured embodiments, mirrors 36 and 38 comprise front-surface reflectors. Alternatively, one or more reflectors of different design, such as a suitable prism with reflective faces, or even transmissive optics, such as a curved light guide, may be used in place of mirrors 36 and 38.

Following reflection from mirrors 36 and 38, beam 54 back-illuminates a sample 56 held by slide 26. Ball lens 40 creates a magnified image of the sample on the image sensor plane in camera module 27. Smartphone 24 captures and processes the image as described further hereinbelow.

Figure 5:
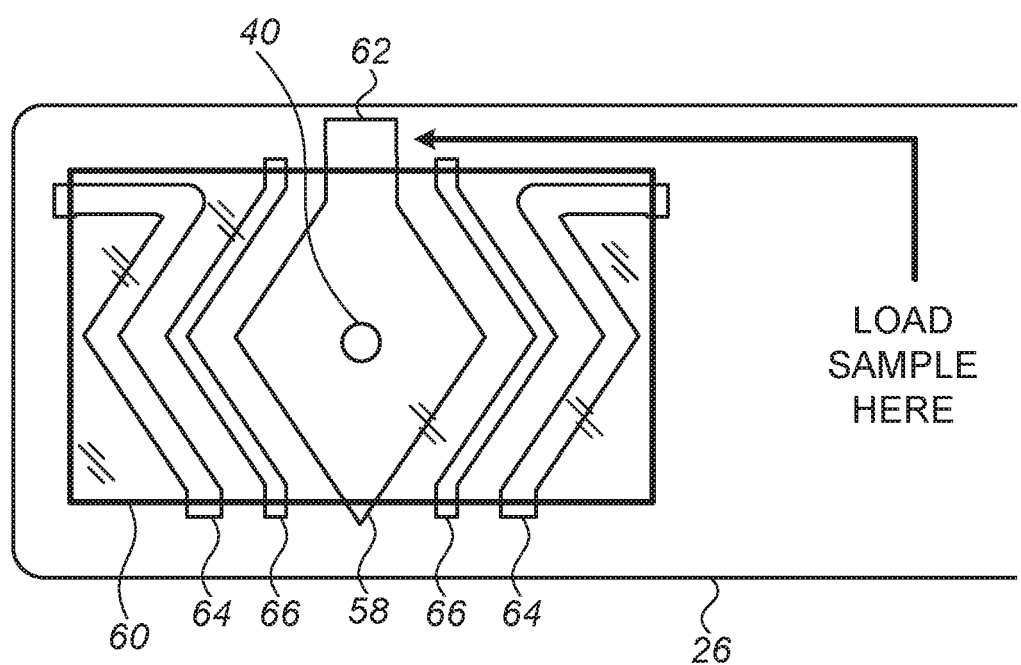
FIG. 5 is a schematic frontal view of a test slide, in accordance with an embodiment of the present invention.

FIG. 5 is a schematic frontal view of test slide 26, in accordance with an embodiment of the present invention. Slide 26 comprises a transparent plastic or glass, which is molded or otherwise manufactured to define a depression 58, typically about 100 μm deep, in the surface of the slide, where the liquid sample is to be held. For example, the depression may alternatively be formed by depositing a layer of a suitable double-sided adhesive, about 100 μm thick, on the surface of the slide around the area that is to hold the sample. A transparent cover slip 60, typically about 0.3 mm thick, is fixed to the slide over the depression (whether molded or formed by double-sided adhesive or other means) so as to define a sample chamber, which is aligned with ball lens 40 as shown in the figure. Cover slip 60 is positioned so as to leave a loading area 62 of depression 58 uncovered. Consequently, when a liquid sample is deposited in loading area 62, the liquid is drawn into the sample chamber by capillary action. Test slide 26 can then be loaded into receptacle 31 for imaging of the sample. The design of test slide 26 ensures that a controlled, known volume of semen will be positioned in the field of view of camera module 27, thus facilitating reliable imaging and assessment.

Typically, cover slip 60 is glued onto slide 26. For this purpose, the slide may be molded to define one or more grooves 64, into which an adhesive is inserted before applying the cover slip to the slide. Once cured (by ultraviolet illumination, for example), the adhesive fixes the cover slip to the slide. To prevent overflow of the adhesive from grooves 64 into the sample chamber, one or more additional grooves 66 may be molded in locations between grooves 64 and depression 58. Alternatively, as noted above, the cover slip may be placed on top of the shaped doublesided adhesive that creates depression 58.

The design of slide 26 and its dimensions are shown and described here by way of example. In alternative embodiments (not shown in the figures), adapter device 22 may accommodate sample holders of other dimensions and designs.

Figure 6:
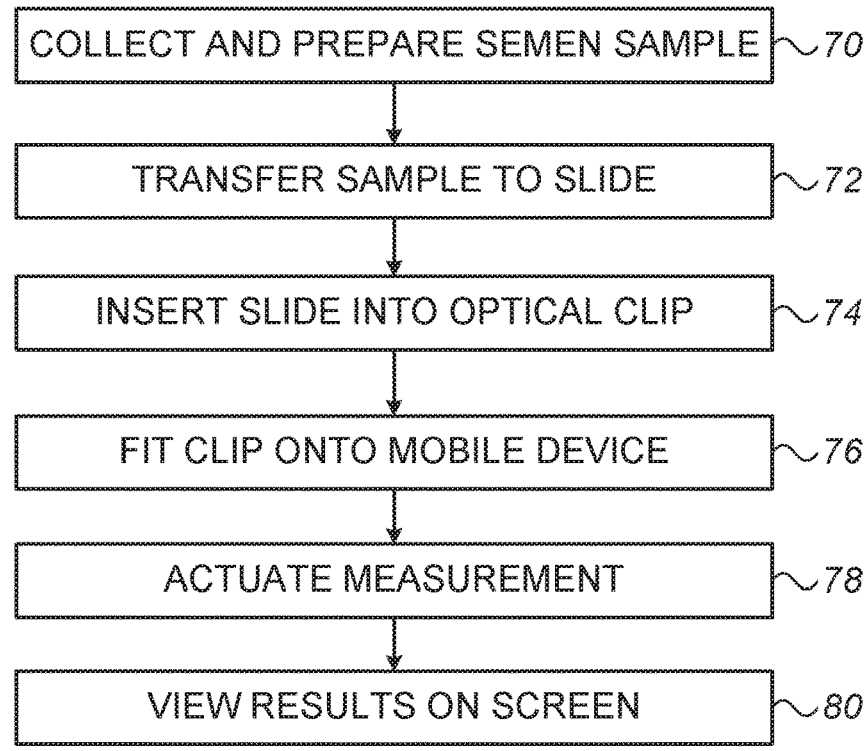
FIG. 6 is a flow chart that schematically illustrates a method for sperm testing, in accordance with an embodiment of the present invention.

FIG. 6 is a flow chart that schematically illustrates a method for sperm testing, in accordance with an embodiment of the present invention. The method is described, for the sake of convenience and clarity, with reference to apparatus 20, but may similarly be applied using mobile computing devices with other sorts of adapters and samples.

The user begins the procedure with the preliminary step of installing testing application software in Smartphone 24. The software may be downloaded from a Web site or "app store," as is known in the art. It includes a user interface, which guides the user in carrying out the test and receives user input as required, as well as drive components to operate camera module 27, light source 29, and display screen 28 as needed. The application software also includes image processing and analysis components, which analyze the images of the sample that are captured by the camera module and compute the test results.

Once the application has been installed, the user collects and prepares a semen sample, at a sample preparation step 70. For this purpose, the user may mix the semen with a liquefying agent, such as chymotrypsin, to reduce its viscosity. The user inserts a small amount of the sample into loading area 62, at a sample transfer step 72, whereupon the sample is drawn into the chamber defined by depression 58, at a sample transfer step 72. For example, the user may draw a small amount of the liquefied semen into a capillary tube, and then place the end of the capillary tube in the loading area so that the semen fills the sample chamber.

The user inserts slide 26 with the sample into receptacle 42 of optical adapter device 22, so that the slide is held firmly in place, at a slide insertion step 74. The user then clips device 22 over the end of Smartphone 24, as shown in the preceding figures, at a device fitting step 76. Alternatively, the order of steps 74 and 76 may be reversed. In either case, the sample is now ready for imaging.

The user indicates to the testing application on Smartphone 24 that the sample is in position by pressing a control presented on screen 28, at a measurement actuation step 78. This step causes the application to turn on light source 29 and operate camera module 27 to capture one or more images of the sample. The image processing component of the application causes the processor in Smartphone 24 to process the electronic images in the mobile computing device so as to compute and output an assessment of the sample. The processing performed at this step is described in greater detail hereinbelow with reference to FIG. 7.

Upon completion of processing the captured images, Smartphone 24 outputs the results, typically via display screen 28, at a data output step 80. The measurement results, such as the MSC, may be output as a numerical value. Alternatively or additionally, it may be preferable simply to report the range in which the result falls, so as to indicate to the user viewing the display whether or not there is cause for concern. For example, in the case of MSC, the result may be reported to the user as "normal" if it is no less than 6 million/ml, or as "low" if the result is below 6 million/ml. In the latter case, the user may be prompted to run the test again, and to see a doctor if the MSC is again found to be low.

Figure 7:
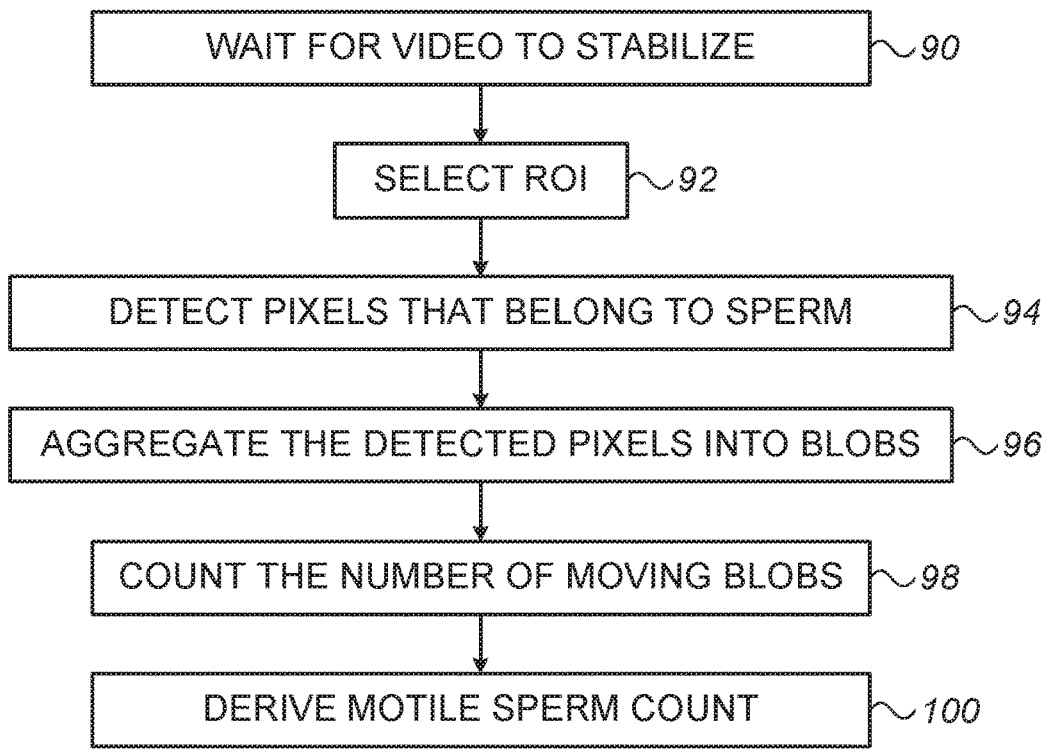
FIG. 7 is a flow chart that schematically illustrates a method for automatic evaluation of motile sperm concentration, in accordance with an embodiment of the present invention.

FIG. 7 is a flow chart that schematically illustrates a method for automatic evaluation of sperm motility, in accordance with an embodiment of the present invention. This method is initiated when the user actuates the measurement process at step 78 (FIG. 6). As noted above, at this step, light source 29 begins to operate, and camera module 27 captures a sequence of images of the backlit sample, typically at a high-resolution setting. Smartphone 24, operating under the control of the above-mentioned application software, waits for the resulting video images to stabilize, at a stabilization step 90. Waiting for stabilization is helpful because the Smartphone auto-focus feature requires time to acquire an optimal video focus while the camera module is running. The Smartphone processor may simply wait for a predefined time, such as 20 seconds, at step 90. Alternatively, the application program may receive feedback from camera module 27 indicating that the auto-focus has locked, and only at that point will it begin capturing images for analysis.

Within the stable video image, the Smartphone processor chooses the area that presents the clearest view of the sperm cells for analysis, at a region of interest (ROI) selection step 92. The inventors have found that an ROI of 700×700 pixels is convenient for analysis and gives reliable results. The processor attempts to select an ROI with good focal quality and contrast. For this purpose, for example, the processor may seek the maximal gradient of gray-level change at every pixel over time (over all processed image frames) and determine the maximum gradient over all the pixels. The processor identifies all pixels in the captured video stream that had a gradient of at least 50% of the maximal gradient at least once in the image sequence. The ROI is then chosen to be the area of 700×700 pixels that is centered at the center of gravity of all of the identified high-gradient pixels.

The application program next causes the Smartphone processor to detect pixels within the ROI that may belong to sperm cells, at a pixel detection step 94. Pixels belonging to sperm cells are defined as dark pixels surrounded by an area of brighter pixels. These dark pixels are detected by first defining the brightness of the background environment and of the areas that are suspected to contain sperm cells, and then this brightness criterion to sort the pixels in the images.

The processor aggregates the potential sperm pixels that it has detected into blobs, at a pixel aggregation step 96. This step may use image processing methods that are known in the art for identification of connected components. Typically, groups of adjoining sperm pixels are labeled to identify them as "blobs," and the blobs are filtered by size, so that only blobs of a certain minimum size are classified as sperm cells. In each image, the processor marks the center of each blob that satisfies these criteria.

The processor counts the number of moving sperm in each image frame by comparing the location of each blob relative to its location in the preceding frame, at a movement counting step 98. If a given blob is found to have moved, the sperm movement count is incremented by one. The total number of blobs that have moved thus gives the movement count for each frame. The processor then computes the motile sperm count based on the median count of moving blobs per image frame, at a motility counting step 100. This value is scaled by the volume of semen contained in the ROI in order to give the actual MSC value, as defined above. The result is output to screen 28 at step 80 (FIG. 6).

Alternatively, other methods of image processing that are known in the art may be applied in analyzing the sequence of images of the sample captured by camera module 27. These alternative methods, as well as the method described above, may be applied not only in computing MSC, but also in extracting measures of sperm count and/or motility alone, as well as analyzing other qualities of semen and other sorts of samples.

Although the embodiments described above refer specifically to sperm testing, and more particularly to assessment of MSC, the principles of the present invention may similarly be applied in testing samples of other sorts, using the capabilities of existing mobile computing devices. It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A method for testing, comprising:
   capturing a sequence of video images of a sample comprising semen; and
   analyzing the sequence of video images by a processor so as to compute and output a motile sperm concentration of the sample,
   wherein analyzing the sequence of video images comprises:
   detecting, in each video image, dark pixels surrounded by areas of brighter pixels;
   aggregating adjoining groups of the detected dark pixels into blobs without identifying individual spermatozoa, each of the blobs comprising a plurality of sperm cells;
   identifying respective locations of each of the blobs in a first image in the sequence of video images; and
   comparing respective locations of each of the blobs in a second image and all subsequent image frames in the sequence of video images to the respective locations of each of the blobs in the first image.

2. The method according to claim 1, wherein the sequence of video images is captured by a camera module in a mobile computing device, and wherein analyzing the sequence of video images comprises processing the captured video images using application software running on the processor in the mobile computing device.

3. The method according to claim 2, wherein analyzing the sequence of video images comprises presenting an assessment of the sample on a display screen of the mobile computing device.

4. The method according to claim 1, wherein analyzing the sequence of video images comprises selecting a region of interest (ROI) within the images, and detecting dark pixels surrounded by areas of brighter pixels within the ROI.

5. The method according to claim 4, wherein selecting the ROI comprises computing gradients of gray—level change at pixels in the images, and choosing a region of maximal gradient values as the ROI.

6. The method according to claim 5, wherein choosing the region comprises identifying all pixels in the captured video images that had a gradient of at least 50% of a maximal gradient at least once in the sequence, and centering the ROI at a center of gravity of the identified pixels.

7. The method of claim 1, wherein analyzing the sequence of video images further comprises filtering the blobs by size to exclude blobs below a predefined minimum size.

8. The method of claim 1, wherein analyzing the sequence of video images further comprises marking the center of each of the blobs, and wherein comparing respective locations of each of the blobs comprises comparing respective locations of the center of each of the blobs.

9. The method of claim 1, further comprising comparing respective locations of each of the blobs in further images in the sequence of video images to the respective locations of each of the blobs in a preceding image.

10. The method according to claim 9, further comprising determining, based on the location comparisons, a number of filtered blobs comprising a plurality of spermatozoa in the second and further images that have moved, and computing, based in part on the number of filtered blobs that have moved, an integral digital signal that is converted into the motile sperm concentration of the sample, without identifying individual spermatozoa.

11. The method according to claim 10, wherein the motile sperm concentration is computed as the integral digital signal generated by the number of the blobs comprising a plurality of spermatozoa that have moved in each of the images in the sequence, scaled by a volume of the semen in a region of the sample analyzed by the processor.

12. Testing apparatus, comprising:
    a camera module, which is configured to capture a sequence of video images of a sample comprising semen; and
    a processor, which is configured to analyze the sequence of video images using a signal processing algorithm so as to compute and output a motile sperm concentration of the sample,
    wherein the processor is configured to analyze the sequence of video images by:
    detecting, in each video image, dark pixels surrounded by areas of brighter pixels;
    aggregating adjoining groups of the detected dark pixels into blobs without identifying individual spermatozoa, each of the blobs comprising a plurality of sperm cells;
    identifying respective locations of each of the blobs in a first image in the sequence of video images and
    comparing respective locations of each of the blobs in a second image and subsequent captured image frames in the sequence of video images to the respective locations of each of the blobs in the first image.

13. The apparatus according to claim 12, comprising a mobile computing device, which comprises the camera module, wherein the sequence of video images is processed using application software running on the processor it the mobile computing device.

14. The apparatus according to claim 13, wherein the mobile computing device comprises a display screen, and the processor is configured to present an assessment of the sample on the display screen.

15. The apparatus according to claim 12, wherein the processor is configured to select a region of interest (ROI) within the images, and to detect sperm cells within the ROI.

16. The apparatus according to claim 15, wherein the processor is configured to select the ROI by computing gradients of gray-level change at pixels in the images, and choosing a region of maximal gradient values as the ROI.

17. The apparatus according to claim 16, wherein the processor is configured to identify all pixels in the captured video images that had a gradient of at least 50% of a maximal gradient at least once in the sequence, and to center the ROI at a center of gravity of the identified pixels.

18. The apparatus of claim 12, wherein the processor is configured to compare respective locations of each of the blobs in further images in the sequence of video images to the respective locations of each of the blobs in a preceding image.

19. The apparatus according to claim 18, wherein the processor is further configured to analyze the sequence of video images by determining, based on the location comparisons without identification of individual sperm cells, a number of filtered blobs comprising a plurality of spermatozoa in the second and further images that have moved, and computing, based in part on the number of filtered blobs that have moved, an integral digital signal that is converted into the motile sperm concentration of the sample.

20. The apparatus according to claim 19, wherein the motile sperm concentration is computed as a median of the number of the blobs that have moved in each of the images in the sequence, scaled by a volume of the semen in a region of the sample analyzed by the processor.

\* \* \* \* \*